(12) United States Patent
Star et al.

(10) Patent No.: US 7,547,931 B2
(45) Date of Patent: Jun. 16, 2009

(54) NANOELECTRONIC CAPNOMETER ADAPTOR INCLUDING A NANOELECTRIC SENSOR SELECTIVELY SENSITIVE TO AT LEAST ONE GASEOUS CONSTITUENT OF EXHALED BREATH

(75) Inventors: Alexander Star, Albany, CA (US); Jeffrey Wyatt, Berkeley, CA (US); Vikram Joshi, San Francisco, CA (US); Joseph R. Stetter, Hayward, CA (US); George Grüner, Los Angeles, CA (US)

(73) Assignee: Nanomix, Inc., Emeryville, CA (US)

( * ) Notice: Subject to any disclaimer, the term of this patent is extended or adjusted under 35 U.S.C. 154(b) by 760 days.

(21) Appl. No.: 11/019,792

(22) Filed: Dec. 20, 2004

(65) Prior Publication Data
US 2005/0245836 A1    Nov. 3, 2005

Related U.S. Application Data

(63) Continuation-in-part of application No. 10/940,324, filed on Sep. 13, 2004, and a continuation-in-part of application No. 10/656,898, filed on Sep. 5, 2003, now abandoned.

(60) Provisional application No. 60/564,248, filed on Apr. 20, 2004, provisional application No. 60/531,079, filed on Dec. 18, 2003.

(51) Int. Cl.
*G01N 1/00* (2006.01)
(52) U.S. Cl. ............... 257/253; 257/E51.04; 977/720; 361/226
(58) Field of Classification Search ............ 257/E51.04, 257/253; 361/226; 977/720, 721, 723
See application file for complete search history.

(56) References Cited

U.S. PATENT DOCUMENTS 3,860,430 A    1/1975 Walker et al.

(Continued)

FOREIGN PATENT DOCUMENTS

EP    1558933    8/2005

(Continued)

OTHER PUBLICATIONS

"Gas and Humidity Sensors Based on Iron Oxide-Polyprrole Nanocomposites", By Suri, K. et al., Sensors and Actuators B 81 (2002) 277-282.

(Continued)

*Primary Examiner*—Thomas L Dickey
(74) *Attorney, Agent, or Firm*—Weaver Austin Villeneuve & Sampson LLP

(57) ABSTRACT

A capnometer adaptor includes a nanostructure sensor configured to selectively respond to a gaseous constituent of exhaled breath, such as to carbon dioxide. In certain embodiments, the adaptor includes an airway adaptor having at least one channel configured for the passage of respiratory gas; at least one nanostructure sensor in fluid communication with the passage, the sensor configured to selectively respond to at least one gaseous constituent of exhaled breath comprising carbon dioxide; and electronic hardware connected to the nanostructure sensor and configured to provide a signal indicative of a response of the sensor to the at least one gaseous constituent of exhaled breath. The sensor may be provided as a compact and solid-state device, and may be adapted for a variety of respiratory monitoring applications.

26 Claims, 7 Drawing Sheets

U.S. PATENT DOCUMENTS

| | | | |
|---|---|---|---|
| 4,795,968 | A | 1/1989 | Madou et al. |
| 4,851,195 | A | 7/1989 | Matthews et al. |
| 4,935,345 | A | 6/1990 | Guilbeau et al. |
| 5,246,859 | A | 9/1993 | Nelson et al. |
| 5,382,417 | A | 1/1995 | Haase |
| 5,425,869 | A | 6/1995 | Noding et al. |
| 5,618,496 | A | 4/1997 | Hasumi et al. |
| 5,674,752 | A | 10/1997 | Buckley et al. |
| 5,827,997 | A | 10/1998 | Chung et al. |
| 5,958,340 | A | 9/1999 | Meyer et al. |
| 5,993,694 | A | 11/1999 | Ito et al. |
| 6,010,459 | A | 1/2000 | Silkoff et al. |
| 6,031,454 | A | 2/2000 | Lovejoy et al. |
| 6,055,447 | A | 4/2000 | Weil et al. |
| 6,090,545 | A | 7/2000 | Wohlstadter et al. |
| 6,111,280 | A | 8/2000 | Gardner et al. |
| 6,136,962 | A | 10/2000 | Shi et al. |
| 6,217,828 | B1 | 4/2001 | Bretscher et al. |
| 6,286,226 | B1 | 9/2001 | Jin |
| 6,287,874 | B1 | 9/2001 | Hefti |
| 6,320,295 | B1 | 11/2001 | McGill et al. |
| 6,346,189 | B1 | 2/2002 | Dai et al. |
| 6,465,132 | B1 | 10/2002 | Jin |
| 6,489,394 | B1 | 12/2002 | Andros |
| 6,528,020 | B1 | 3/2003 | Dai et al. |
| 6,577,242 | B2 | 6/2003 | Jen et al. |
| 6,656,712 | B1 | 12/2003 | Balavoine et al. |
| 6,676,904 | B1 | 1/2004 | Lee et al. |
| 6,797,325 | B2 | 9/2004 | Wang et al. |
| 6,894,359 | B2 | 5/2005 | Bradley et al. |
| 7,109,859 | B2 | 9/2006 | Peeters |
| 7,271,720 | B2 | 9/2007 | Tabe |
| 2002/0117659 | A1 | 8/2002 | Lieber et al. |
| 2002/0118027 | A1 | 8/2002 | Routkevitch et al. |
| 2002/0130333 | A1 | 9/2002 | Watanabe et al. |
| 2003/0031620 | A1 | 2/2003 | Harutyunyan et al. |
| 2003/0041438 | A1 | 3/2003 | Wei et al. |
| 2003/0068432 | A1 | 4/2003 | Dai et al. |
| 2003/0134267 | A1 | 7/2003 | Kang et al. |
| 2003/0134433 | A1 | 7/2003 | Gabriel et al. |
| 2003/0139003 | A1 | 7/2003 | Gole et al. |
| 2003/0171257 | A1 | 9/2003 | Stirbl et al. |
| 2003/0171781 | A1 | 9/2003 | Florio et al. |
| 2003/0175161 | A1 | 9/2003 | Gabriel et al. |
| 2003/0180640 | A1 | 9/2003 | Darty |
| 2004/0011291 | A1 | 1/2004 | Delaunay et al. |
| 2004/0018587 | A1 | 1/2004 | Makowski et al. |
| 2004/0023428 | A1 | 2/2004 | Gole et al. |
| 2004/0029297 | A1 | 2/2004 | Bonnell et al. |
| 2004/0043527 | A1 | 3/2004 | Bradley et al. |
| 2004/0065970 | A1 | 4/2004 | Blanchet-Fincher |
| 2004/0091285 | A1 | 5/2004 | Lewis |
| 2004/0104129 | A1 | 6/2004 | Gu et al. |
| 2004/0120183 | A1 | 6/2004 | Appenzeller et al. |
| 2004/0132070 | A1 | 7/2004 | Star et al. |
| 2004/0136866 | A1 | 7/2004 | Pontis et al. |
| 2004/0158410 | A1 | 8/2004 | Ono et al. |
| 2004/0188780 | A1 | 9/2004 | Kurtz |
| 2004/0192072 | A1 | 9/2004 | Snow et al. |
| 2004/0200734 | A1 | 10/2004 | Co et al. |
| 2004/0202603 | A1 | 10/2004 | Fischer et al. |
| 2004/0211580 | A1 | 10/2004 | Wang et al. |
| 2005/0072213 | A1 | 4/2005 | Besnard et al. |
| 2005/0112052 | A1 | 5/2005 | Gu et al. |
| 2005/0129573 | A1 | 6/2005 | Gabriel et al. |
| 2005/0157445 | A1 | 7/2005 | Bradley et al. |
| 2005/0184641 | A1 | 8/2005 | Armitage et al. |
| 2005/0245836 | A1 | 11/2005 | Star et al. |
| 2005/0279987 | A1 | 12/2005 | Star et al. |
| 2006/0021881 | A1 | 2/2006 | Soundarrajan et al. |
| 2006/0054936 | A1 | 3/2006 | Lieber et al. |
| 2006/0055392 | A1 | 3/2006 | Passmore et al. |
| 2006/0555392 | | 3/2006 | Passmore et al. |
| 2006/0263255 | A1 | 11/2006 | Han et al. |
| 2007/0048180 | A1 | 3/2007 | Gabriel et al. |
| 2007/0048181 | A1 | 3/2007 | Chang et al. |
| 2007/0114573 | A1 | 5/2007 | Han et al. |
| 2007/0132043 | A1 | 6/2007 | Bradley et al. |
| 2007/0208243 | A1 | 9/2007 | Gabriel et al. |
| 2008/0021339 | A1 | 1/2008 | Gabriel et al. |
| 2008/0093226 | A1 | 4/2008 | Briman et al. |
| 2008/0221806 | A1 | 9/2008 | Bryant et al. |

FOREIGN PATENT DOCUMENTS

| | | |
|---|---|---|
| EP | 1664724 | 6/2006 |
| EP | 1680353 | 7/2006 |
| EP | 1941270 | 7/2008 |
| JP | 2005-507121 | 11/2003 |
| JP | 2007-505323 | 3/2007 |
| WO | WO97/32571 | 9/1997 |
| WO | WO01/32951 | 5/2001 |
| WO | WO01/44796 | 6/2001 |
| WO | WO02/15240 | 2/2002 |
| WO | WO02/079514 | 10/2002 |
| WO | WO02/095099 | 11/2002 |
| WO | WO03/016901 | 2/2003 |
| WO | WO03/046536 | 6/2003 |
| WO | WO03/078652 | 9/2003 |
| WO | WO2004/044586 | 5/2004 |
| WO | WO2005/026694 | 3/2005 |
| WO | WO2005/062031 | 7/2005 |
| WO | WO2005/094221 | 10/2005 |
| WO | WO2007/114931 | 10/2007 |
| WO | WO2007/136523 | 11/2007 |
| WO | WO2008/039165 | 4/2008 |
| WO | WO2008/052104 | 5/2008 |

OTHER PUBLICATIONS

U.S. Appl. No. 11/390,493, filed Mar. 27, 2006, Ben-Barak et al.
U.S. Appl. No. 11/924,328, filed Oct. 25, 2007, Bryant et al.
European Search Report dated Mar. 30, 2007 issued in EP04788761.
PCT Preliminary Examination Report dated Nov. 16, 2006 issued in WO2004044586.
PCT International Search Report dated Mar. 20, 2004 issued in WO2004044586.
PCT International Search Report dated Sep. 22, 2005 issued in WO2005026694.
PCT International Search Report dated Nov. 6, 2007 issued on WO2005094221.
PCT Preliminary Examination Report and Written Opinion dated Nov. 6, 2007 issued in WO2005094221.
PCT International Search Report dated Jun. 11, 2008 issued in WO 2008/052104.
PCT International Written Opinion dated Jun. 11, 2008 issued in WO2008/052104.
PCT International Search Report and Written Opinion dated Jun. 11, 2008 issued in WO2008039165.
PCT Preliminary Examination Report and Written Opinion dated Sep. 22, 2005 issued in WO2005026694.
US Office Action dated Jun. 1, 2005 issued in U.S. Appl. No. 10/940,324.
US Office Action dated Mar. 3, 2006 issued in U.S. Appl. No. 10/940,324.
US Office Action dated Sep. 7, 2006 issued in U.S. Appl. No. 10/940,324.
US Office Action Final dated Feb. 21, 2007 issued in U.S. Appl. No. 10/940,324.
US Office Action dated Aug. 27, 2007 issued in U.S. Appl. No. 10/940,324.
US Examiner Interview Summary dated Feb. 1, 2008 issued in U.S. Appl. No. 10/940,324.
US Office Action Final dated May 27, 2008 issued in U.S. Appl. No. 10/940,324.

US Office Action dated Aug. 12, 2008 issued in U.S. Appl. No. 10/940,324.
US Office Action dated Dec. 2, 2005 issued in U.S. Appl. No. 10/945,803.
US Office Action Final dated Apr. 6, 2007 issued in U.S. Appl. No. 10/945,803.
US Office Action Final dated Sep. 12, 2007 issued in U.S. Appl. No. 10/945,803.
US Office Action dated Jun. 12, 2008 issued in U.S. Appl. No. 10/945,803.
US Notice of Allowance dated Jul. 7, 2008 issued in 10/945,803.
US Office Action dated Mar. 17, 2006 issued in U.S. Appl. No. 10/656,898.
US Office Action Final dated Oct. 20, 2006 issued in U.S. Appl. No. 10/656,898.
US Office Action dated May 7, 2007 issued in U.S. Appl. No. 10/656,898.
US Office Action Final dated Jan. 17, 2008 issued in U.S. Appl. No. 10/656,898.
US Advisory Action dated Apr. 8, 2008 issued in U.S. Appl. No. 10/656,898.
US Office Action dated Jul. 24, 2008 issued in U.S. Appl. No. 10/656,898.
US Office Action Final dated Jan. 24, 2007 issued in U.S. Appl. No. 10/704,066.
US Office Action dated Jun. 1, 2006 issued in U.S. Appl. No. 10/704,066.
US Office Action dated Aug. 24, 2007 issued in U.S. Appl. No. 10/704,066.
US Office Action—Examiner Summary dated Mar. 6, 2008 issued in U.S. Appl. No. 10/704,066.
US Office Action dated Dec. 12, 2007 issued in U.S. Appl. No. 10/655,529.
US Office Action Final dated Jul. 3, 2008 issued in U.S. Appl. No. 10/655,529.
US Advisory Action dated Sep. 22, 2008 issued in U.S. Appl. No. 10/655,529.
US Office Action dated Feb. 25, 2008 issued in U.S. Appl. No. 11/274,747.
US Office Action dated May 25, 2008 issued in U.S. Appl. No. 11/274,747.
US Office action dated Apr. 1, 2008 issued in U.S. Appl. No. 11/111,121.
US Examiner Interview Summary dated Sep. 23, 2008 issued in U.S. Appl. No. 11/111,121.
US Notice of Allowance and Examiner's Amendment dated Oct. 8, 2008 issued in U.S. Appl. No. 11/111,121.
US Office Action dated Apr. 16, 2008 issued in U.S. Appl. No. 11/488,456.
US Office Action dated Jul. 14, 2008 issued in U.S. Appl. No. 11/019,792.
US Office Action dated Jul. 24, 2008 issued in U.S. Appl. No. 11/390,493.
US Office Action dated Oct. 3, 2008 issued in U.S. Appl. No. 11/400,038.
Collins (2001), "Current Saturation and Electrical breakdown in Multiwalled Carbon Nanotubes," *Phys. Rev. Lett.*, v.86, 3127-3131.
Collins (2001), "Engineering Carbon Nanotubes and Nanotube Circuits Using Electrical Breakdown," *Science*, 292, 706-709.
Cui et al., "Nanowire Nanosensors for highly sensitive and selective detection of biological and chemical species," *Science 293*, (2001) p. 1289-1292, May. 7, 2001.
Dai, H. (2002) "Carbon nanotubes: opportunities and challenges," *Surface Science*, 500:218-241.
Deng et al. (2001), "Hybrid Composite of Polyaniline Containing Carbon nanotube," Chinese chemical Ltrs, vol. 12, pp. 1037-1040.
Derycke et al. (Sep. 2001) "Carbon Nanotube Inter- and Intramolecular Logic Gates," *Amer. Chem Soc Lets*, 1(9):453-456.
Kong (2001), "Functionalized Carbon Nanotubes for Molecular Hydrogen sensors," *Adv. Mater*, 13:1384-1386.
Lin, Yi et al. (2002) "Functionalization Multiple-Walled Carbon Nanotubes with Aminopolymers," *Jnl of Phy Chem,B, Materials, Surfaces, Interfaces and Biophysical*, Washington DC U.S. 106(6)1294-1298; XP002971880.
Ng, HT et al. (Dec. 2001) "Flexible carbon nanotube membrane sensory system: a generic platform", *Journal of Nanoscience and Nanotechnology*, 1(4):375-379.
Shim et al (2002) "Functionalization of Carbon Nanotubes for Biocompatibility and Biomolecular Recognition," *Nano Letter*, 2(4):285-288, Published on Web Jan. 25, 2002.
Shim et al. (2001), "Polymer Functionalization for Air-Stable n-Type Carbon Nanotube Field-Effect Transistors," Jnl Am.Chem Soc., v123 pp. 11512-11513.
Simon (2001) "Micromachined metal Oxide gas sensors: opportunities to improve sensor performance," Sensors and Actuators, v73, pp. 1-26.

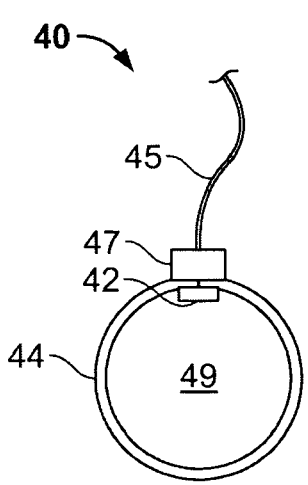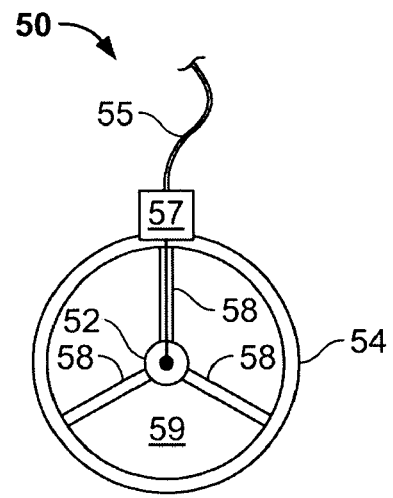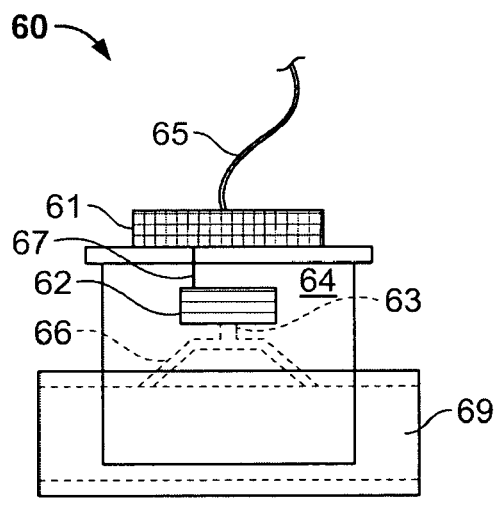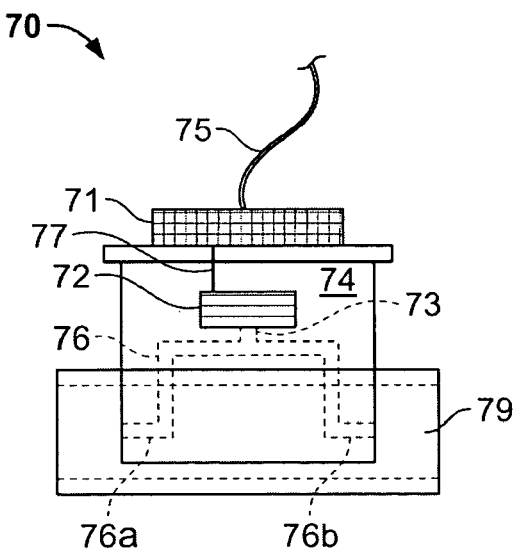
FIG. 4
FIG. 5
FIG. 6
FIG. 7

NANOELECTRONIC CAPNOMETER ADAPTOR INCLUDING A NANOELECTRIC SENSOR SELECTIVELY SENSITIVE TO AT LEAST ONE GASEOUS CONSTITUENT OF EXHALED BREATH

CROSS-REFERENCE TO RELATED APPLICATIONS

This application claims priority pursuant to 35 U.S.C. § 119(e) to Provisional Application No. 60/531,079, filed Dec. 18, 2003, entitled "Nanoelectronic Capnometer Adapter," and to Provisional Application No. 60/564,248, filed Apr. 20, 2004, entitled "Remotely Communicating, Battery-Powered Nanostructure Sensor Devices". This application is a continuation-in-part of patent application Ser. No. 10/940,324, filed Sep. 13, 2004, entitled "Carbon Dioxide Nanoelectronic Sensor," and of patent application Ser. No. 10/656,898, filed Sep. 5, 2003 now abandoned, entitled "Polymer Recognition Layers For Nanostructure Sensor Devices." Each of the above-identified provisional and non-provisional patent applications is specifically incorporated herein, in its entirety, by reference.

BACKGROUND OF THE INVENTION

1. Field of the Invention

The present invention relates to an apparatus and method for mainstream patient airway medical monitoring, such as by using a capnometer.

2. Description of Related Art

The measurement of carbon dioxide levels in respiration is a standard procedure during intensive care and anesthesia and is a primary tool in the diagnosis and management of respiratory function. A need in this medical monitoring is to measure and track $CO_2$ concentration in the breath, sometimes referred to as capnography.

To meet the necessary specifications of such capnography device, current technology relies on bulky and expensive non-dispersive infrared absorption (NDIR) sensors to determine $CO_2$ concentration. The high cost and limitations of this technology restrict the use of capnography to high value, controlled environments, such as surgical wards. In addition, it has been shown that capnography is particularly important in determining the proper placement of endotracheal tubes in emergency medical response.

There are two approaches to implement this detection method, mainstream and sidestream. Mainstream devices make use of a sensor located at the patient airway by means of an airway adapter. In contrast, sidestream device requires connection of a sample line to the airway, and a sensor located away from the patient. Notwithstanding the advantages of these approaches, each may be subject to certain limitations that may compromise the effectiveness of $CO_2$ monitoring.

A comparison of exemplary limitations of prior-art apparatus and methods are listed below:

Mainstream
Secretions and humidity block the sensor.
A heating element is used to negate condensation.
A bulky device is at the patient airway.
The sensor must be sterilized and calibrated after each use.
The sensor is not usable with non-intubated patients.
Sidestream
Secretions block sample tubing.
A necessity for a water trap.
A slower response for $CO_2$ changes.
Reduced air flow decreases tidal volume.
Additional sample tubing.
A costly pump and suction system.

It is desirable, therefore, to provide an apparatus and method for monitoring $CO_2$ or other gases in a patient's airway, that overcomes the limitations of the prior art.

SUMMARY OF THE INVENTION

The present invention overcomes the limitations of the prior art using a novel capnometer apparatus. A nanoelectronic capnometer system having aspects of the invention offers: (i) performance that matches or exceeds that of infrared technology, (ii) plug-and-play simplicity in a disposable package, (iii) the small size and low power consumption needed for wireless integration and (iv) the ability to incorporate arrays of sensors on a single chip. This $CO_2$ sensing technology offers an order of magnitude reduction in the cost of the sensor component.

The capnometer comprises a nanoelectronic gas sensor integrated into an airway adapter for mainstream capnometry. The nanoelectronic sensor may comprise a solid-state nanotube or other nanostructure sensor, for example, as described in the parent application Ser. No. 10/940,324. The capnometer apparatus may further comprise an appropriate adapter fitting that maximizes sensor performance. Both the adaptor fitting and the sensor may be incorporated into a compact and relatively low-cost assembly. Instead of sterilizing the capnometer after use, the sensing unit may be discarded, thereby avoiding difficulties and costs associated with sterilization.

The nanoelectronic gas sensor may be configured to respond to a chemical of interest, for example, carbon dioxide, oxygen or anesthesia gases. It may be integrated into a fitting designed to be inserted into an intubated or non-intubated patient airstream, such as, for example, during anesthesia application and/or respiratory monitoring. The nanoelectronic gas sensor ("nanosensor") itself may comprise a small packaged solid-state device incorporating a nanstructure sensor that is exposed to airflow on the inside of the tube and electronically connected to the outside of the tube. The fitting together with the enclosed nanosensor may be designed as a disposable device. A potentially reusable external electronics package that contains signal processing electronics may be socketed or snapped into place to make a secure connection with the sensor. This electronics module may include a microprocessor, memory cell, power supply (including a battery) and a wired or wireless connection to a monitor where the sensor output is stored and/or displayed.

Being extremely small with a nanometer-scale active sensing area, the sensor may readily be protected from contamination, and can therefore be located in the more desirable mainstream configuration for faster response times. At the same time, the low cost of the chip-scale sensor can make it possible to dispose the sensor and its associated adaptor after each use, thereby eliminating the problem of disinfection. The capnometer adaptor with its sensor may be very compact, cost-effective and convenient to use in a clinical setting. It is anticipated, therefore, that the invention will greatly facilitate and enhance the beneficial practice of capnography.

One exemplary capnometer embodiment having aspects of the invention comprises: an airway adaptor having at least one channel configured to permit the passage of respiratory gas; at least one solid-state nanostructure sensor arranged adjacent the airway adaptor in communication with the passage, the sensor having a sensitivity to at least one gaseous constituent of exhaled breath; electronic circuitry connected to the solid state sensor and configured to receive at least a signal indicative of the concentration of the at least one gaseous constituent of exhaled breath; and an output device connected to the electronic circuitry and configured to provide at least one of a qualitative and a quantitative measure of the concentration of the at least one gaseous constituent of exhaled breath. Preferably, the at least one gaseous constituent of exhaled breath includes carbon dioxide and the solid-state sensor incorporates a nanostructure as a sensing element responsive to the at least one gaseous constiuent.

In certain embodiments, the at least solid-state nanostructure sensor comprises: a substrate; a first nanostructure over the substrate; at least two conducting elements in electrical communication with the first nanostructure; and at least one recognition material operatively associated with the first nanostructure, the at least one recognition material configured for interacting with carbon dioxide.

In alternative embodiments, the airway adaptor is configured to be mated so as to transmit at least a portion of the exhalation flow of at least a one of: a respirator/resuscitation system, a endotracheal ventilator system, an sleep apnea treatment system, a sleep apnea diagnostic system, an anesthesia system, a cardiac function diagnostic system, a metabolic function measuring system, an asthma monitoring system, and a gastro-intestinal testing system.

A more complete understanding of the capnometer adaptor will be afforded to those skilled in the art, as well as a realization of additional advantages and objects thereof, by a consideration of the following detailed description of the preferred embodiment. Reference will be made to the appended sheets of drawings which will first be described briefly.

BRIEF DESCRIPTION OF THE DRAWINGS

FIG. 4 is a schematic diagram showing a capnometer sensor and adaptor with remote electronics, wherein the sensor is disposed directly in the airstream of the adaptor fitting.

FIG. 5 is a schematic showing an exemplary alternative structure for an adaptor and sensor of the type shown in FIG. 4, wherein the sensor is disposed in the airstream.

FIG. 6 is a schematic diagram showing a side view of a capnometer sensor and adapter generally similar to that shown in FIGS. 1A and 1B, but having a sensor arranged adjacent a secondary parallel lumen in communication with the airway passage.

FIG. 7 is a schematic diagram showing a side view of a capnometer sensor and adapter generally similar to that shown in FIG. 6, but having inlet and outlet ends of the secondary parallel lumen projecting into airway passage into the exhalation flow path.

DETAILED DESCRIPTION OF THE PREFERRED EMBODIMENT

The embodiment of the invention incorporates a nanoelectronic capnometer into an adapter for patient airway monitoring. The resulting device seamlessly integrates into a mainstream capnography setup and delivers performance advantages over that of today's mainstream and sidestream NDIR capnometers.

FIGS. 1-7 depict a number of different embodiments, in which the same or generally similar elements are identified by numbers, in which the last digit corresponds to the equivalent or corresponding element, as much as possible, in each figure, with the digits preceding the last digit corresponding to the figure number of each example embodiment.

Figure 1A:
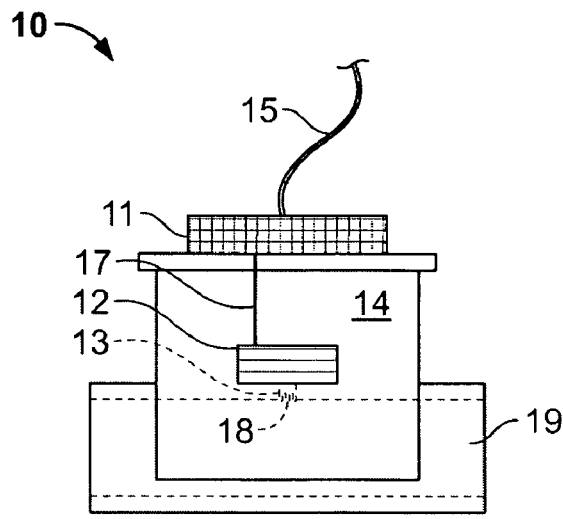
FIGS. 1A and 1B are schematic diagrams showing a wired capnometer sensor and adapter system from side and tube views, respectively.
Figure 1B:
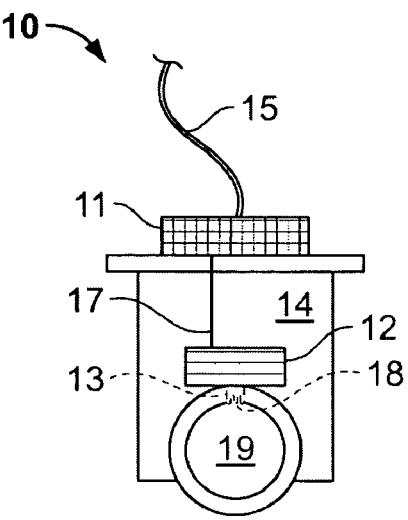

Referring to FIGS. 1A and 1B, in an exemplary embodiment having aspects of the invention, the unit may be configured like conventional airway adapters, with an input and output for connecting tubing to an air channel 19 running through a housing 14. One opening of housing 14 may be fed by the patient's respiration and the other opening may be connected to the breathing or anesthesia circuit. The adapter 10 may be connected to a power and signal cable 15. Cable 15 may be used to relay gas monitoring data to the display unit, as well as powering the sensor. The cable may be directly connected to an electronics module 11. This module may be configured for signal processing, analysis, and delivery of data values/waveforms to users. Module 11 contain a microprocessor with embedded software and backup battery power. The electronics module may be located above and connected by connector 17 to a solid-state sensor 12 (e.g., a nanoelectronic capnometer sensor such as is disclosed in application Ser. No. 10/940,324). Module 11 may be configured to readily detach and reattach, facilitating replacement of the sensor-containing adapter 14. Electronics module 11 and sensor 12 may be provided on a single unitary semiconductor device, for example, a silicon chip, if desired.

The nanoelectronic sensor 12 may be disposed in fluid communication with respired air passing through channel 19. In order to provide a sample volume to the capnometer, a small window or opening 13 may be provided between the sensor 12 and channel 19. The sample window may be provided with membranes and/or filters 18 to reduce condensation, block patient secretions, and overall maintain stability of the sensor. For example a gas-permeable hydrophobic membrane, e.g. a PFC membrane, may be used.

When using a nanotube electronic sensor, it is not necessary to maintain a clear optical path between a transmitter and receiver, unlike prior-art NDIR sensors for carbon dioxide sensing. Furthermore, the active sensing area of a nanotube sensor is extremely small, so one may readily protect the sensor from contamination in the patient airstream. For example, very little power is required to heat the sensor to a stable temperature at which condensation is prevented. And the sensor may be protected from non-volatile contaminants by a simple mechanical filter and/or gas permeable membrane, which need only be large enough to minimize the likelihood of excessive filter blockage during the anticipated life of the sensor. For reusable sensors, filter units may be removed and disposed between use, and then replaced with a new filter unit. For most applications, however, it may be desirable to dispose and replace the entire unit 10, including any associated filters.

The unit 10 may be comprised primarily of a mechanically stable housing 14. Housing 14 may be comprised of any suitable plastic or other material with similar chemical and physical properties for use in medical tube fittings, as known in the art.

The capnometer sensor 12 may be based on nanoscale components as described in the parent patent application Ser. No. 10/940,323 and herein, for selectively sensing carbon dioxide. Sensing of other gases may also be achieved using a suitably configured nanotube sensor, for example, a sensor as described in U.S. provisional applications Ser. No. 60/457,697 filed March 2003 and Ser. No. 60/468,621 filed May 2003, and U.S. non-provisional applications Ser. No. 10/177,929 filed June, 2002, Ser. No. 10/656,898 filed Sep. 5, 2003, Ser. No. 10/655,529 filed Sep. 4, 2003, Ser. No. 10/388,701 filed Mar. 14, 2003, and Ser. No. 10/345,783 filed Jan. 16, 2003; each of which is incorporated herein by reference.

Sensing for two or more gases, for example, carbon dioxide and oxygen, may be accomplished using one or more sensors like sensor 12. A single sensor may include a plurality of nanotube sensors, each configured to sense a different gas. In addition, or in the alternative, a plurality of nanotube sensors may be each configured to sense the same gas, for purposes of redundancy. It should be appreciated that the extremely small scale of a nanotube sensor makes it possible to cost-effectively incorporate numerous nanometer-scale sensors in a single gas sensing unit 12, which may essentially consist of a very compact silicon chip or other device. In the alternative, one or more nanotube sensing devices may be assembled together into a sensing unit with multiple sensors. Since each device may be quite small, space and/or cost need not be limiting concerns.

Figure 2:
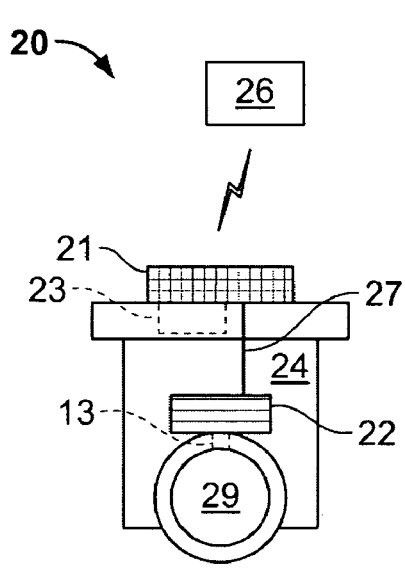
FIG. 2 is a schematic diagram showing a wireless capnometer sensor and adapter system from an end view relative to the tube fitting.

A capnometer according to the invention may readily be configured to operate wirelessly. FIG. 2 shows a wireless unit 20 without a need for a power or signal cable. To compensate for this alteration, one can implement wireless communication capabilities into the electronics module 21 for wireless communication to a base station 26. Since the capnometer 22 uses little power, an on-board miniature battery 23 may provide sufficient power for its lifetime. Housing 24 and channel 29 may be configured similarly as in capnometer 10.

Figure 3:
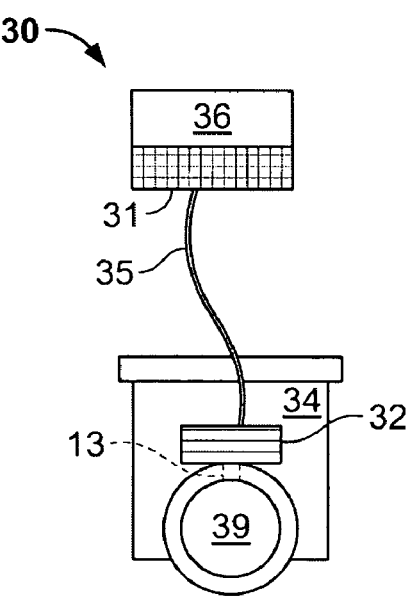
FIG. 3 is a schematic diagram showing a wired capnometer sensor and adapter system with all electronics remote from the sensor, from an end view relative to the tube fitting.

In the alternative, a capnometer 30 may be designed to function with all electronics 31 separate from the sensor 32, as shown in FIG. 3. Here the sensor 32 has a cable that connects it to the electronics module 31, which is located remotely. For example, module 31 may be incorporated into a display and base station 36, which may be reused with different capnometer units 30. Base station 36 may then incorporate more complex hardware and software for capnography, for example, display or analysis systems. Signal and power cord 35 to the sensor may be removably connected to unit 30, allowing only the sensor unit 30 to be discarded and replaced.

It also is desirable to provide disposable capnometer sensing adaptors, wherein the sensing package is installed directly in the main air channel of the respiratory stream. FIGS. 4 and 5 show exemplary embodiments of this type. FIG. 4 shows a capnometer sensing and airflow adaptor unit 40, comprising a tubular adaptor 44 with internal air channel 49. Nanoelectric unit 42 may be mounted to the wall of channel 49, and connected to a cable connector 47 mounted on the outside of adaptor 44 by a wire. It is possible, for example, to integrate sensing unit 42 and its connecting wires into the adaptor 44 during a plastic molding process, thereby minimizing the possibility for leakage into or out of channel 49 adjacent to the sensor 42. Sensor 42 may comprise a nanotube device as described above. It may be protected from contamination by a suitable filter and/or gas-permeable membrane (not shown) disposed around or over the sensor. For example, one may encapsulate sensor 12 in a gas-permeable membrane material, and/or a suitable filter and/or membrane may be separately mounted in channel 49.

Alternatively, one may dispose the sensing unit more directly in the airstream. For example, FIG. 5 shows a capnometer sensor and adaptor 50, wherein a nanoelectric sensor 52 is mounted in the center of channel 59 using a plurality of ribs 58. Ribs 58 may be molded integrally with sensor 52 and/or adaptor housing 54, with a molded-in connection to cable 55. In the alternative, ribs 58 and sensor 52 may comprise a sub-assembly that is later assembled in housing 54. Such a sub-assembly may attach to a molded-in electrical connector (not shown) passing through the wall of housing 54. It should be apparent that either design would virtually eliminate the possibility for inaccurate sensor readings from outside air leakage. Ribs 58 or any other suitable mounting structures for sensor 52 may also be used to hold protective filters and membranes around sensor 52. Such a design may be particularly suitable for monitoring respiration from a subject in blow-testing equipment such as used for blood-alcohol testing and the like.

FIG. 6 is a schematic diagram showing a side view of a capnometer sensor and adapter 30 generally similar to that shown in FIGS. 1A and 1B, but having a sensor 62 arranged adjacent a secondary parallel lumen 66 in communication with the airway passage 69. Window or opening 63 communicates to parallel lumen 66 directly, and is in only indirect communication with passage 69.

FIG. 7 is a schematic diagram showing a side view of a capnometer sensor and adapter generally similar to that shown in FIG. 6, but having inlet and outlet ends 66a and 76b of the secondary parallel lumen 76 projecting into airway passage 79 into the exhalation flow path.

Note that the examples of FIGS. 6 and 7 show the parallel lumen arranged close to the adaptor housing and primary passage. Alternatively, the parallel lumen may be extended, so that senor, electronic circuitry, displays, and/or data memory are located remotely from the airway.

Embodiments of this invention include a new sensing technology for carbon dioxide ($CO_2$) that uses nanoelectronic components. A tiny, low-cost nanosensor chip can offer: (i) performance that matches or exceeds that of infrared technology, (ii) plug-and-play simplicity with both digital and analog control systems, and (ii) the small size and low power consumption needed for wireless integration.

Figure 8:
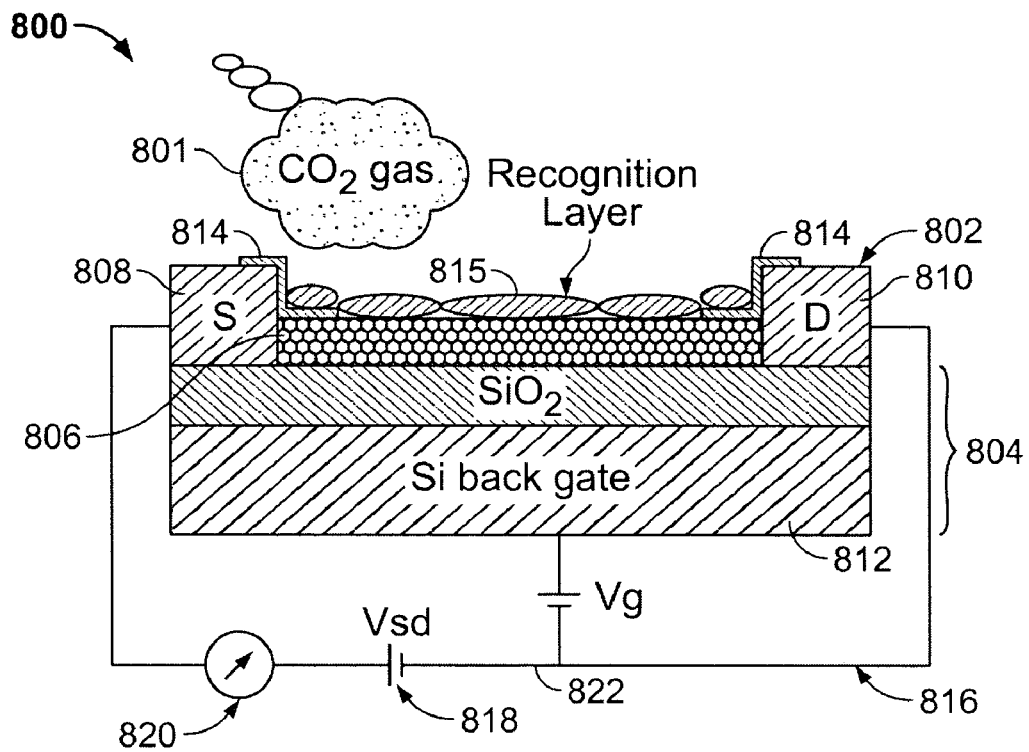
FIG. 8 is a schematic diagram showing an exemplary nanostructure sensor for use with the invention.

Field effect transistors made from semiconducting single-walled carbon nanotubes (NTFETs) have been used as the platform for sensitive chemical sensors. FIG. 8. shows an electronic system 800 for detecting carbon dioxide 801, comprising a nanostructure sensing device 802. Device 802 comprises a substrate 804, and a nanostructure 806 disposed over the substrate. The nanostructure may contact the substrate as shown, or in the alternative, may be spaced a distance away from the substrate, with or without a layer of intervening material. In an embodiment of the invention, nanostructure 806 may comprises a carbon nanotube. Any other suitable nanostructure, such as a nanowire, nanofiber, or nanorod, may also be used. In addition, or in the alternative, nanostructure 806 may comprise boron, boron nitride, and carbon boron nitride, silicon, germanium, gallium nitride, zinc oxide, indium phosphide, molybdenum disulphide, silver, or any other suitable material. In an alternative embodiment, nanostructure 806 comprises an interconnected network of smaller nanostructures. For example, nanostructure 806 may comprise a plurality of nanotubes forming a mesh.

Two conductive elements 808, 810 may be disposed over the substrate and electrically connected to nanostructure 806. Elements 808, 810 may comprise metal electrodes in direct contact with nanostructure 806. In the alternative, a conductive or semi-conducting material (not shown) may be interposed between elements 808, 810 and nanostructure 806. A functionalization material 815 reactive with carbon dioxide is disposed on nanostructure sensing device 802 and in particular, on nanostructure 806. Material 815 may be deposited in a continuous layer, or in a discontinuous layer. Material 815 may comprise more than one material and/or more than one layer of material.

Device 802 may further comprise a gate 812. Device 802 may further comprise a layer of inhibiting material 814 covering regions adjacent to the connections between the conductive elements 808, 810 and the first nanostructure 806. The inhibiting material may be impermeable to at least one chemical species, such as carbon dioxide. The inhibiting material may comprise a passivation material as known in the art, such as silicon dioxide. Further details concerning the use of inhibiting materials in a NTFET are described in prior application Ser. No. 10/280,265, filed Oct. 26, 2002, which is incorporated by reference herein.

In addition, system 800 may further comprise a second nanostructure sensing device (not shown) like device 802. It may be advantageous to provide the second device with a functionalization layer that incorporates a material different from that incorporated into layer 815.

System 800 may further include a nanostructure sensing device circuit 816. Circuit 816 may include one or more electrical supplies 818, a meter 820 in electrical communication with the electrical supply or supplies 818, and electrical connections 822 between the first nanostructure sensing device 802 and both the electrical supply and the meter. System may further comprise a signal control and processing unit (not shown) as known in the art, in communication with the first nanostructure sensing device circuit.

The carbon nanotube acts not as the sensing element itself but as a sensitive transducer. There are various designs for the basic platform; these include devices with one or only a few nanotubes and devices with a network of nanotubes. A useful nanotube network device architecture has been described in commonly-owned application Ser. No. 10/177,929, filed on Jun. 21, 2002, which is included by reference herein. The nanotube transducers can be chemically functionalized to provide desired sensitivity and selectivity. They can even be made sensitive to a variety of inert gases. The functionalization approach relies on the ability of basic inorganic compounds and organic polymers as well as aromatic compounds with electron-donating functionalities to provide electrons to nanotubes, thus resulting in n-doping of NTFETs.

Sensitivity to $CO_2$ can be achieved through functionalization also. The functionalization layer has two main functions: 1) it selectively recognizes carbon dioxide molecules and 2) upon the binding of $CO_2$ it generates an amplified signal that is transferred to the carbon nanotube transducer. In the presence of water, carbon dioxide forms carbonic acid which dissociates and alters the pH of the functionalization layer, thus protonating the electron donating groups and making the NTFET more p-type. Basic inorganic compounds (e.g., sodium carbonate), pH-sensitive polymers, such as polyaniline, poly(ethyleneimine), poly(o-phenylenediamine), poly (3-methylthiophene), and polypyrrole, as well as aromatic compounds (benzylamine, naphthalenemethylamine, antracene amine, pyrene amine, etc.) can be used to functionalize NTFETs for $CO_2$ sensing. The functionalization layer can be constructed using certain polymeric materials such as polyethylene glycol, poly(vinyl alcohol) and polysaccharides, including various starches as well as their components amylose and amylopectin.

Materials in the functionalization layer may be deposited on the NTFET using various different methods, depending on the material to be deposited. For example, inorganic materials, such as sodium carbonate, may be deposited by drop casting from 1 mM solution in light alcohols. The functionalized sensor may then be dried by blowing with nitrogen or other suitable drying agent. Polymeric materials may be deposited by dip coating. A typical procedure may involve soaking of the chip with the carbon nanotube device in 10% polymeric solution in water for 24 hours, rinsing with water several times, and blowing the chip dry with nitrogen. Polymers which are not soluble in aqueous solutions may be spin coated on the chip from their solutions in organic solvents. Values of polymer concentrations and the spin coater's rotation speeds may be optimized for each polymer. Further details pertaining to polymer recognition layers may be described in commonly-owned parent application Ser. No. 10/658,898, filed Sep. 5, 2003, which is also incorporated by reference herein.

Figure 9:
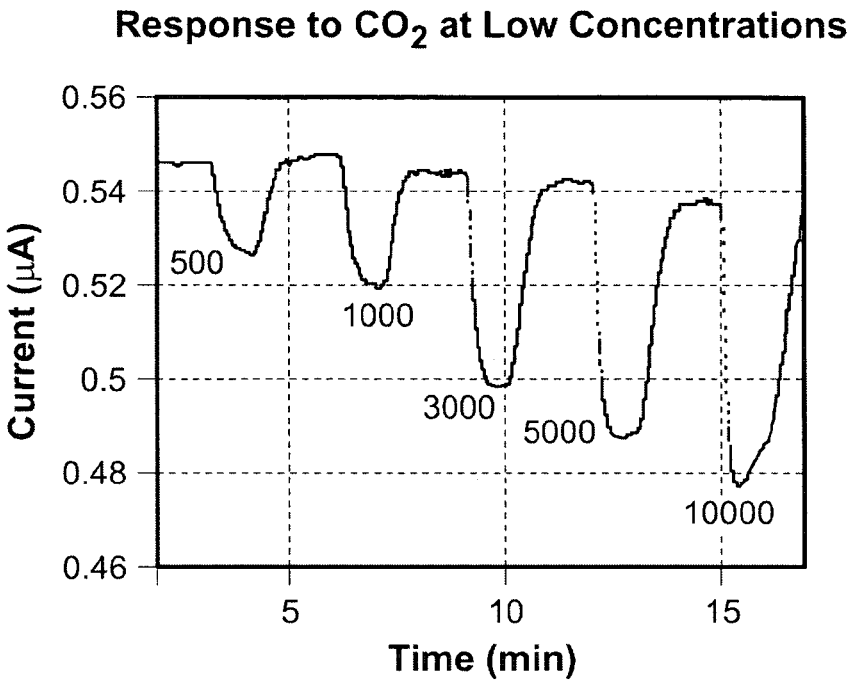
FIG. 9 is a plot showing the response of an exemplary nano-electronic carbon dioxide sensor to a range of low concentrations of carbon dioxide in air.

FIG. 9 is a plot showing the response of an exemplary nano-electronic carbon dioxide sensor to a range of low concentrations of carbon dioxide in air. The response to $CO_2$ gas is fast and reproducible at different concentrations.

Figure 10:
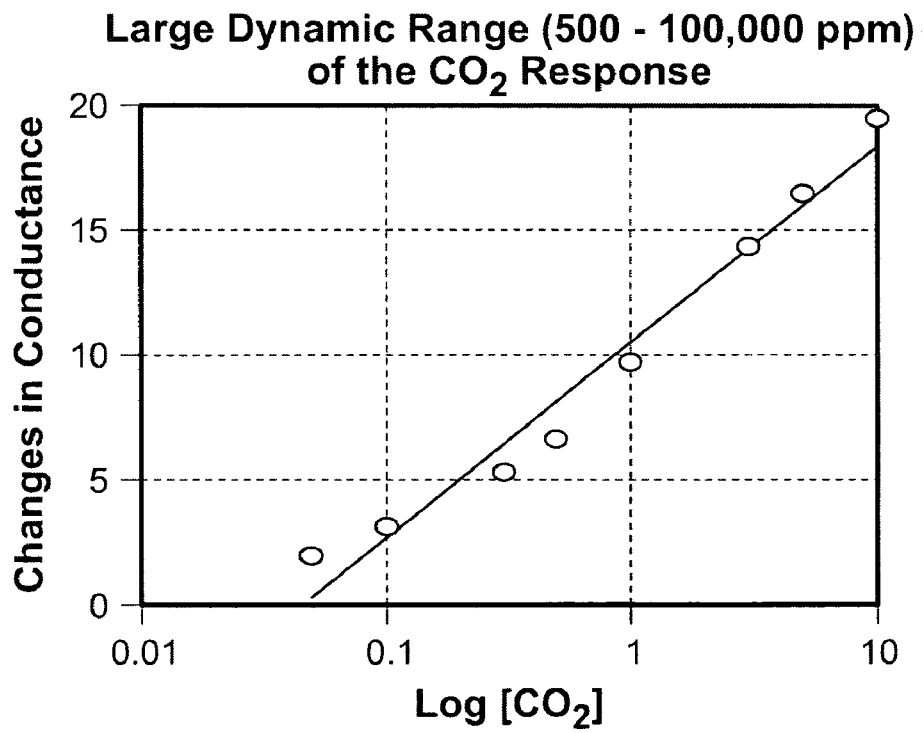
FIG. 10 is a plot showing the response of an exemplary nano-electronic carbon dioxide sensor to a wide range concentrations of carbon dioxide in air.

FIG. 10 is a plot showing the response of an exemplary nano-electronic carbon dioxide sensor to a wide range concentrations of carbon dioxide in air. The sensor shows wide dynamic range in the concentration range of 500-100,000 ppm (0.5%-10%). Suitable recognition chemistry and specificity permit the sensor to operate at different relative humidities and shows low cross-sensitivity to anesthesia gases (oxygen and nitrous oxide).

Figure 11:
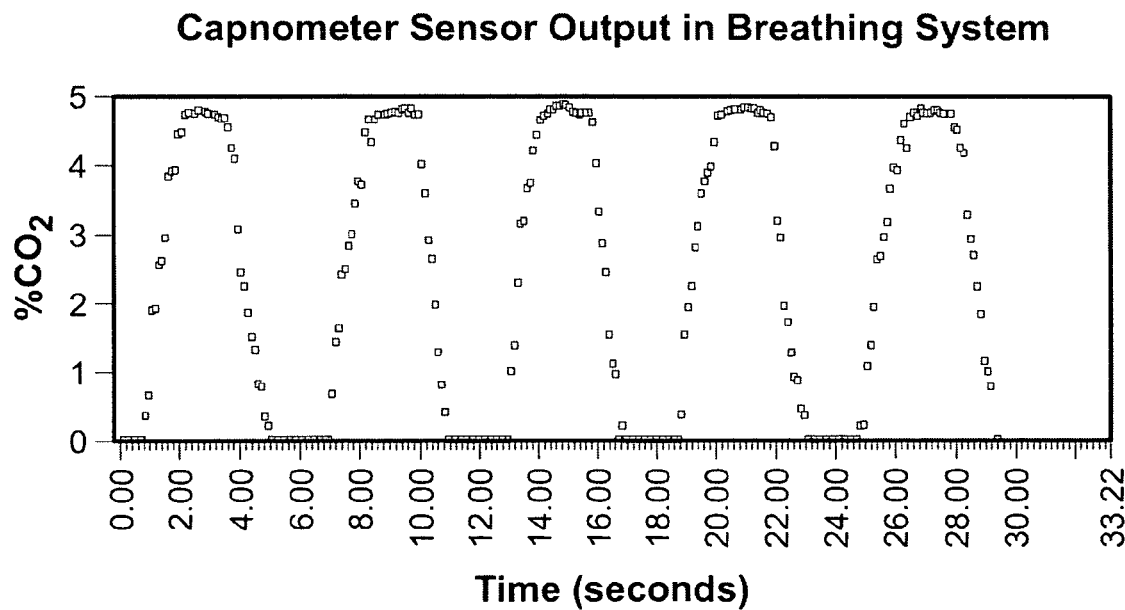
FIG. 11 is a plot showing the response of an exemplary capnometer having aspects of the invention to simulated human breathing.

FIG. 11 is a capnogram plot showing the response of an exemplary capnometer having aspects of the invention to simulated human breathing. The performance of the sensor at this clinically relevant condition shows the great potential for these sensors in capnography and anesthesia medical applications.

Capnometers having aspect of the invention may be included in many different sorts of medically useful system, both as permanent, semi-disposable, or completely disposable components. Likewise, a variety of different arrangements of the sensors, signal and power circuitry and data display and recordation subsystems are practical.

Figure 12A:
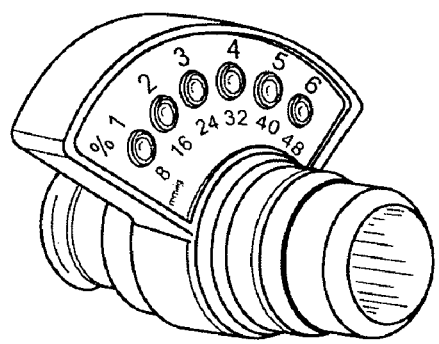
FIGS. 12A, 12B and 12C depict exemplary configurations of a capnometer adaptor, in which the output device is mounted to the adapter housing and displays a quantitative bar graph.
Figure 12B:
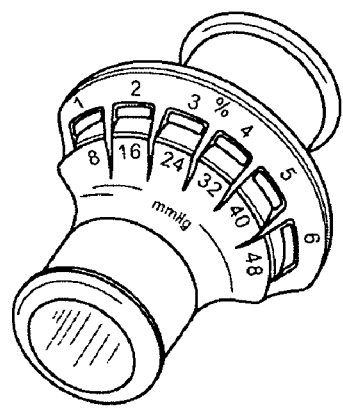
Figure 12C:
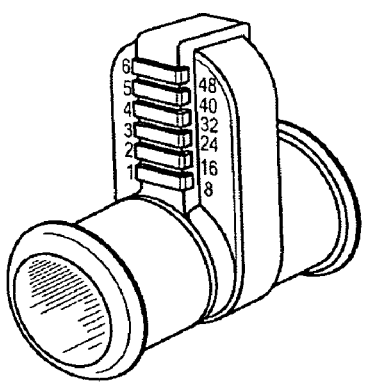

FIGS. 12A, 12B and 12C depict exemplary configurations of capnometer adaptors 120, 121, and 122 having aspects of the invention, in which the output device is mounted to the adapter housing and displays a quantitative bar graph.

Figure 13:
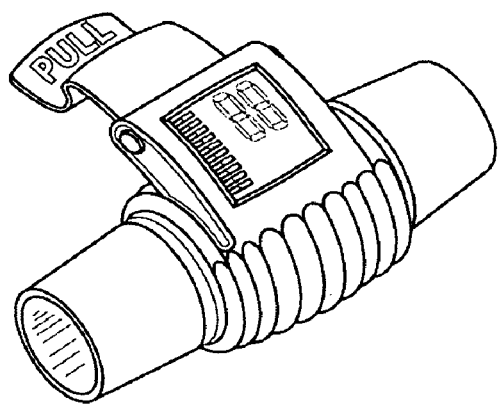
FIG. 13 depicts an exemplary configuration of a capnometer adaptor, in which the output device is mounted to the adapter housing and displays a both a digital reading and a quantitative bar graph.

FIG. 13 depicts exemplary configurations of a capnometer adaptor 130 having aspects of the invention, in which the output device is mounted to the adapter housing and displays a both a digital reading and a quantitative bar graph.

Figure 14:
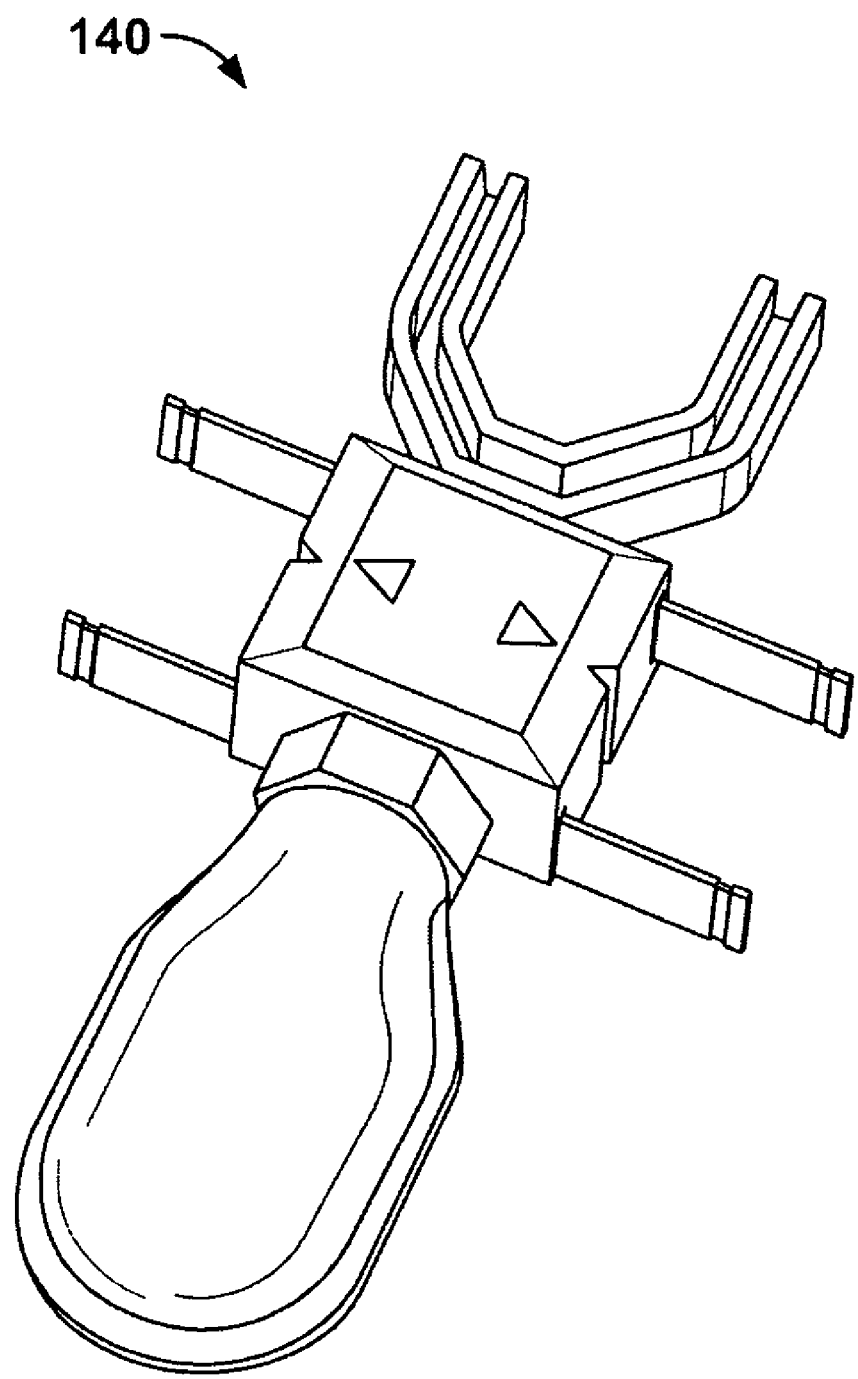
FIG. 14 depicts an exemplary capnometer adaptor configured to mate with a nasal canula, and to communicate with external data logging circuitry (not shown).

FIG. 14 depicts exemplary configurations of a capnometer adaptor 140 having aspects of the invention, in which capnometer adaptor is configured to mate with a nasal canula, and to communicate with external data logging circuitry (not shown).

Figure 15A:
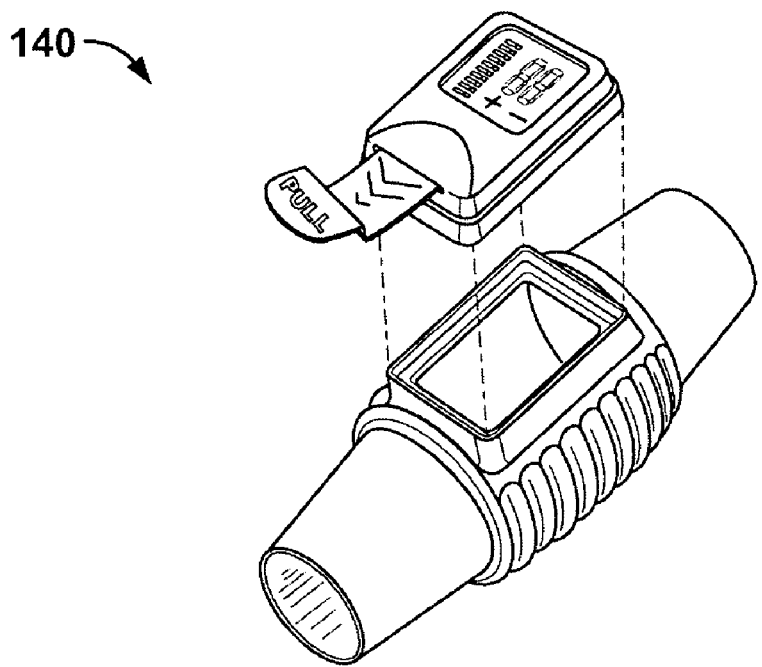
FIGS. 15A and 15B depict exemplary configurations of a capnometer adaptor, in which either one or both of the sensor and the electronic circuitry is separately detachable from the airway adaptor housing.
Figure 15B:
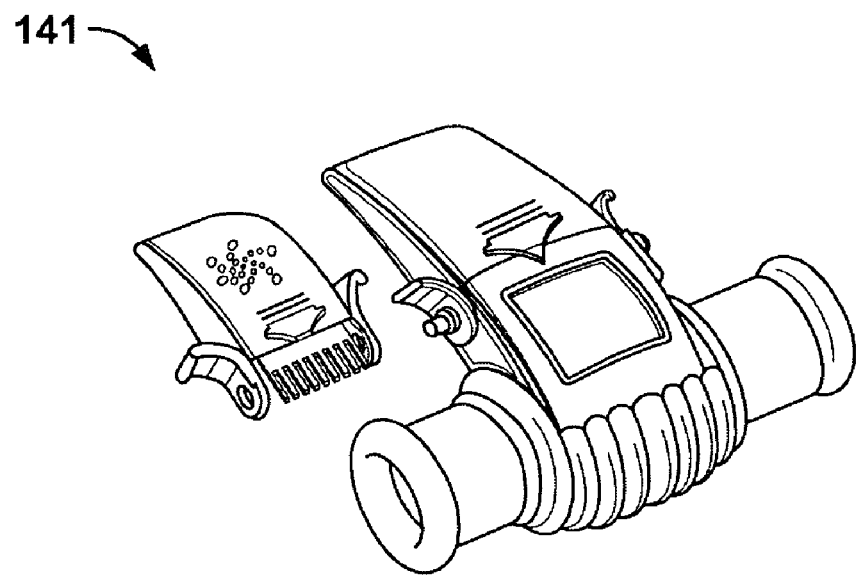

FIGS. 15A and 15B depict exemplary configurations of capnometer adaptors 150, 151 having aspects of the invention. In adaptor 150, both of the sensor and the electronic circuitry are separately detachable from the airway adaptor housing. In adaptor 151, the electronic circuitry is separately detachable from the airway adaptor housing without removing the sensor.

Note that capnometers having aspects of the invention may include a wide variety of data acquisition, storage, processing and output devices. For example, the capnometer signal may be used to determine respiration rate, and inhaled gas composition, in addition to exhaled breath composition, such as end-tidal $CO_2$ values. In addition to discrete point values, a real-time and continuous profile of breath composition may be determined and displayed, e.g as a plot of $CO_2$ concentration versus time.

Additional Medical Applications

Capnometers having aspects of the invention can be embedded into standard embodiments for breath monitoring commonly found in emergency medicine, ex: airway adapters, masks, ambubags, and laryngeal masks etc. The construction of the sensor assembly is flexible to address most airway monitoring environments. The sensor may be used in hospital, prehospital, and out-of-hospital settings, so as to provide highly valuable monitoring information to all health care providers whether they are doctors, nurses, respiratory technicians or EMTs.

Among the applications where the capnometers having aspects of the invention could provide significant healthcare benefits are:

Endotracheal Tube Verification

Breathing Quality Assessment

Intra and Inter-Hospital Transport

Adequacy of CPR

Table 1 shows example specifications of a disposable capnometer adapter having aspects of the invention, configured to provide a typical Emergency Medical Services/Emergency Department with a small, noninvasive, and disposable in-line sensor that continuously monitors varying $CO_2$ levels and delivers accurate measurement of end tidal carbon dioxide concentrations. For example, the device may have a bar graph to continuously track $CO_2$ concentration. The operating lifetime of the sensor, 6 hours, is more than sufficient to accommodate long transport times.

TABLE 1

| Specification: | Example: |
|---|---|
| Technology | Nanotube Sensor |
| Display | Bar Graph |
| Range | 0-6% (0-48 mm Hg) |
| Resolution | 1% (8 mm Hg) |
| Response Time | 500 ms |
| Shelf Life | 1 Year |
| Use Life | 6 Hours |

Additional applications include:

Anesthesia-Capnography—used to monitor adequacy of ventilation, verification of proper intubation and quality of respiration during surgical procedures requiring anesthesia. It also applies to post-op, intensive care and critical care monitoring.

Emergency Medical Services/Emergency Department— An end tidal CO2 value is a predictor of cardiac output and an indicator of adequate respiration. Many situations in the EMS could benefit from reporting of this value: cardiac arrest, respiratory arrest, trauma, seizures, shock, diabetic ketoacidosis, asthma, intra/inter hospital transport and most importantly, endotracheal tube placement.

Procedural Sedation—The Joint Commission on Accreditation of Healthcare Organizations (JCAHO) has supported the continuous monitoring of respiration during sedation. Patients receiving care at offices should be given equal care as in the operating room whether intubated or nonintubated, including tracking expired CO2 values for patents.

Asthma—Monitoring of CO2 can assess the severity of a bronchospasm and notify successful medication or treatment.

Sleep Apnea—The monitoring of CO2 levels can be used to screen for apnea, the stoppage of breathing. In addition to diagnostic applications, CO2 monitoring can show efficacy of therapeutic machines.

Metabolic Testing—Various types of metabolic testing track expired CO2 levels and volumes as a means to garner a metabolic assessment, including one's resting metabolic rate.

Gastro-Intestinal Testing—CO2 measurement is needed to monitor and capture alveolar respiratory gas as part of sampling for various breath testing: lactose/fructose intolerance, bacterial overgrowth, and H. Pylori (peptic ulcers).

Having thus described a preferred embodiment of the nanoelectronic capnometer sensor, it should be apparent to those skilled in the art that certain advantages of the within system have been achieved. It should also be appreciated that various modifications, adaptations, and alternative embodiments thereof may be made within the scope and spirit of the present invention. A wide variety of support structure and/or adaptor geometries may be suitable, and the invention is not limited to the particular shapes depicted in the schematic diagrams.

What is claimed is:

1. A capnometer; comprising: an airway adaptor having at least one channel configured for the passage of respiratory gas; at least one nanostructure sensor in fluid communication with the passage, the sensor configured to selectively respond to at least one gaseous constituent of exhaled breath comprising carbon dioxide; electronic hardware connected to the nanostructure sensor and configured to provide a signal indicative of a response of the sensor to the at least one gaseous constituent of exhaled breath;

wherein the at least one nanostructure sensor comprises: a substrate; a first nanostructure over the substrate; at least two conducting elements in electrical communication with the first nanostructure; and at least one recognition material operatively associated with the first nanostructure, wherein the at least one recognition material comprises a material selected from the group consisting of benzylamine, naphthalenemethylamine, antracene amine, and pyrene amine.

2. A capnometer as in claim 1, further comprising an output device connected to the electronic hardware and configured to provide an output indicative of a concentration of the at least one gaseous constituent of exhaled breath.

3. The capnometer of claim 1, wherein the first nanostructure is selected from the group consisting of nanotubes, nanowires, nanofibers, and nanorods.

4. The capnometer of claim 1, wherein the first nanostructure comprises at least one element selected from the group consisting of carbon, boron, boron nitride, and carbon boron nitride, silicon, germanium, gallium nitride, zinc oxide, indium phosphide, molybdenum disulphide, and silver.

5. The capnometer of claim 1, wherein the first nanostructure comprises a single-wall carbon nanotube.

6. The capnometer of claim 1, wherein the conducting elements comprise metal electrodes.

7. The capnometer of claim 1, wherein the conducting elements are in direct physical contact with the first nanostructure.

8. The capnometer of claim 1, wherein the at least one recognition material comprises a plurality of different materials.

9. The capnometer of claim 1, further comprising a gate electrode in proximity to the nanostructure.

10. The capnometer of claim 1, further comprising a layer of inhibiting material covering regions of the sensor adjacent to the connections between the conductive elements.

11. The capnometer of claim 1, wherein the airway adaptor is configured to receive a portion of exhalation flow from at least a one of: a respirator system, a endotracheal ventilator system, an sleep apnea treatment system, a sleep apnea diagnostic system, an anesthesia system, a cardiac function diagnostic system, a metabolic function measuring system, an asthma monitoring system, and a gastro-intestinal testing system.

12. The capnometer of claim 1, wherein the capnometer is configured to mate with one of a respirator mask, an ambubag, and laryngeal mask.

13. The capnometer of claim 1, wherein at least a portion of the capnometer is configured to be disposable.

14. The capnometer of claim 1, wherein the at least one recognition material comprises a substantially continuous layer over the nanostructure.

15. The capnometer of claim 14, wherein the at least one recognition material further comprises a layer of metal disposed adjacent the gate electrode.

16. The capnometer of claim 15, wherein the recognition material further comprises a layer of polymeric material disposed adjacent the layer of metal.

17. The capnometer of claim 1, wherein at least one recognition material further comprises a layer of metal disposed adjacent the first nanostructure.

18. The capnometer of claim 17, wherein the recognition material further comprises a layer of polymeric material disposed adjacent the layer of metal.

19. The capnometer of claim 1, wherein the airway adaptor is configured to receive exhalation flow from at least a one of: a respirator system, a endotracheal ventilator system, an sleep apnea treatment system, a sleep apnea diagnostic system, an anesthesia system, a cardiac function diagnostic system, a metabolic function measuring system, an asthma monitoring system, and a gastro-intestinal testing system.

20. The capnometer of claim 19, wherein the airway adaptor is configured to operate externally to a patient's body.

21. The capnometer of claim 20; wherein the airway adaptor is configured to operate internally to a patients body.

22. A capnometer; comprising: an airway adaptor having at least one channel configured for the passage of respiratory gas; at least one nanostructure sensor in fluid communication with the passage, the sensor configured to selectively respond to at least one gaseous constituent of exhaled breath comprising carbon dioxide; electronic hardware connected to the nanostructure sensor and configured to provide a signal indicative of a response of the sensor to the at least one gaseous constituent of exhaled breath;

wherein the at least one nanostructure sensor comprises: a substrate; a first nanostructure over the substrate; at least two conducting elements in electrical communication with the first nanostructure; and at least one recognition material operatively associated with the first nanostructure, wherein the at least one recognition material comprises poly(ethylene imine) in mixture with a starch.

23. The capnometer of claim 22, wherein the starch comprises at least one of amylose and amylopectin.

24. The capnometer of claim 22, wherein the at least one recognition material further comprises a metallic carbonate.

25. The capnometer of claim 22, wherein the at least one recognition material further comprises at least one carbonate selected from the group consisting of lithium carbonate, sodium carbonate, potassium carbonate, cesium carbonate, barium carbonate, calcium carbonate, and silver carbonate.

26. The capnometer of claim 22, wherein the at least one recognition material further comprises a pH-sensitive polymer.

* * * * *